(12) United States Patent
Tojo et al.

(10) Patent No.: US 8,586,622 B2
(45) Date of Patent: Nov. 19, 2013

(54) LAMININ-332 PRODUCT ON STIMULATING COMPOSITION

(75) Inventors: Yosuke Tojo, Yokohama (JP); Jun-ichi Hosoi, Yokohama (JP); Kayo Matsumoto, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/261,241

(22) PCT Filed: May 14, 2010

(86) PCT No.: PCT/JP2010/058219
§ 371 (c)(1),
(2), (4) Date: Mar. 28, 2012

(87) PCT Pub. No.: WO2011/040082
PCT Pub. Date: Apr. 7, 2011

(65) Prior Publication Data
US 2012/0184593 A1 Jul. 19, 2012

(30) Foreign Application Priority Data

Sep. 30, 2009 (JP) .................. 2009-225871
Sep. 30, 2009 (JP) .................. 2009-225872

(51) Int. Cl.
*A01N 43/36* (2006.01)

(52) U.S. Cl.
USPC ........................................ 514/423; 514/561

(58) Field of Classification Search
USPC ................................. 514/423, 561
See application file for complete search history.

(56) References Cited

U.S. PATENT DOCUMENTS

2002/0009472 A1* 1/2002 Takekoshi et al. ............ 424/401
2007/0237735 A1 10/2007 Denommee

FOREIGN PATENT DOCUMENTS

| JP | 11-060436 A | 3/1999 |
|---|---|---|
| JP | 2001-302417 A | 10/2001 |
| JP | 2003-137768 A | 5/2003 |
| JP | 2003-313135 A | 11/2003 |
| JP | 2004-315384 A | 11/2004 |
| JP | 2005-003558 A | 1/2005 |
| JP | 2006-327972 A | 12/2006 |
| JP | 2008-185558 A | 8/2008 |
| JP | 2009-040757 A | 2/2009 |
| JP | 2009-191039 A | 8/2009 |
| WO | WO 00/51561 A1 | 9/2000 |
| WO | WO 2006/033355 A1 | 3/2006 |
| WO | WO 2006/126385 A1 | 11/2006 |

OTHER PUBLICATIONS

Tetsuji et al, JP1999-060436, published Mar. 2, 1999, Machine Translation.*
Tomoya et al, JP2004-315384, published Nov. 11, 2004, Machine Translation.*
Kinya et al, JP2005-029486, published Feb. 3, 2005, Machine Translation.*
Hiroyasu, JP2009-040757, published Feb. 26, 2009, Machine Translation used.*
Tsunenaga et al, Fragrance Journal, 2008, 36(2), 55-62.*
Aberdam et al., "Herlitz's junctional epidermolysis bullosa is linked to mutations in the gene (LAMC2) for the γ2 subunit of nicein/kalinin (LAMININ-5)," Nature Genetics, Mar. 1994, 6:299-304.
Ahmed et al., "A new rapid and simple non-radioactive assay to monitor and determine the proliferation of lymphocytes: an alternative to [$^3$H]thymidine incorporation assay," Journal of Immunologital Methods, 1994, 170:211-224.
Amano, Satoshi, "Possible Involvement of Basement Membrane Damage in Skin Photoaging," Journal of Investigative Dermatology Symposium Proceedings, 2009, 14:2-7.
Amano, S., "Anti-Ageing Skin Care for Cutaneous Photo-Ageing," SOFW-Journal, Sep. 2008, 134:10-14.
Amano, Satoshi, "A specific and sensitive ELISA for laminin 5," Journal of Immunological Methods, 1999, 224:161-169.
Fitsialos et al., "HIF1 transcription factor regulates laminin-332 expression and keratinocyte migration," Journal of Cell Science, 2008, 121:2992-3001.
Kajiro, Y., Ed., "Amino Acids," Harper's Biochemistry, 22$^{nd}$ Edition, Maruzen Co. Ltd., Tokyo, Mar. 30, 1991, 21-30, with partial English translation of indicated portions, 2 pages.
Kinouchi et al., "D-Amino acid biosystem in mammal," Protein, Nucleic Acids and Enzymes, 2005, 50(5):453-460, with partial English translation of indicated portion, 1 page.
Morikawa et al., "Alterations in D-amino acid levels in the brains of mice and rats after the administration of D-amino acids," Amino Acids, 2007, 32:13-20.
Smola et al., "Dynamics of Basement Membrane Formation by Keratinocyte-Fibroblast Interactions in Organotype Skin Culture," Experimental Cell Research, 1998, 239:399-410.
Sugawara et al., "Laminin-332 and -511 in skin," Experimental Dermatology, 2008, 17:473-480.
Yamashina et al., "Amino Acids, Peptides, and Proteins," Principles of Biochemistry, 2$^{nd}$ Ed., Hirokawa Publishing Co., Tokyo, Apr. 15, 1993, 132-147, with partial English translation of indicated portion, 1 page.
Zboralski et al., "Divergent mechanisms underlie Smad4-mediated positive regulation of the three genes encoding the basement membrane component laminin-332 (laminin-5)," BMC Cancer, 2008, 8:215, 13 pages.

* cited by examiner

*Primary Examiner* — Jason M Sims
*Assistant Examiner* — Ibrahim D Bori
(74) *Attorney, Agent, or Firm* — Foley & Lardner LLP (57) ABSTRACT

Disclosed is a novel composition which has a function of stimulating production of laminin-332. The composition is stable and safe, and can be used routinely. Specifically disclosed is a laminin-332 production stimulating composition which contains one or more compounds selected from the group consisting of D-alanine, D-hydroxyproline, derivatives and/or salts thereof. The composition may be used for the purpose of suppressing and/or improving a skin condition. The skin condition may include, but is not limited to a photoaging, wrinkles, a rough skin, fine wrinkles and a dry skin. The composition may be used for an external preparation for the skin or a food.

5 Claims, 6 Drawing Sheets

LAMININ-332 PRODUCT ON STIMULATING COMPOSITION

CROSS-REFERENCE TO RELATED APPLICATIONS

This application is a National Stage application of PCT/JP2010/058219, filed May 14, 2010, which claims priority from Japanese application JP2009-225871, filed Sep. 30, 2009, and JP 2009-225872, filed Sep. 30, 2009.

TECHNICAL FIELD

The present invention relates to a composition for stimulating laminin-332 production comprising one or more compounds selected from the group consisting of D-alanine and D-hydroxyproline, and derivatives and/or salts thereof, and a method of suppressing and/or improving a skin condition comprising a step of administering the compound.

BACKGROUND ART

Laminin is a trimeric protein composed of three strands including an α (alpha) chain, a β (beta) chain, and a γ (gamma) chain. Based on combination of five types of α (alpha) chain, three types of β (beta) chain, and three types of γ (gamma) chain, at least fifteen isomers are known to be present. Among them, laminin-332 (α3β3γ2 (alpha 3 beta 3 gamma 2), i.e., laminin-5 according to previous nomenclature) is found in great amount in the basal membrane which is present between epidermis and dermis, and it is believed to play an important role for maintaining structure and function of the skin (Non-Patent Document 1). Laminin-332 knockout mice demonstrated separation of the epidermis from the dermis to form vesicles, exhibiting the phenotype which is identical to junctional epidermolysis bullosa, i.e., a human hereditary disorder, and as a result laminin-332 was proven to be essential for adhesion of epidermis on the dermis (Non-Patent Document 2). Further, when a purified sample of laminin-332 is added to a skin equivalent model in which keratinocytes are cultured on a collagen gel embedded with human fibroblasts, the basal membrane formation is enhanced (Non-Patent Document 3). Plasmin is a protease for activated proteins produced by epidermal cells and it cleaves off laminin-332 α (alpha) 3 subunit amino terminal peptide and the carboxy terminal peptide, and β (beta) 3 subunit amino terminal peptide. Each of the cleaved fragments includes a recognition site for substrate adhesion molecule in the cell and a binding site for type VII collagen. Thus, the laminin-332 obtained by digestion with plasmin reduces adhesion ability for keratinocytes. Further, the laminin-332 obtained by digestion with plasmin lowers affinity for type VII collagen. For such reasons, it is believed that skin aging caused by UV irradiation or others are involved in the digestion of laminin-332 by plasmin and impaired function of a basal membrane caused thereby (Non-Patent Document 4).

Thus, by stimulating laminin-332 production, there is a possibility of suppressing and/or improving the skin aging caused by UV irradiation or others. With respect to the factors which stimulate laminin-332 production, it has been recently reported that HIF1 (Non-Patent Document 5) and Smad4 (Non-Patent Document 6) induce transcription of α (alpha) 3 subunit gene. However, HIF1 is a transcription regulator which responds to an environmental stimulation like lack of oxygen and mechanical stimulation, and it is also up-regulated by a proinflammatory cytokine. Smad4 is a transcription regulator involved with signal transduction of TGF-β (beta). All of these regulators are proteins with high molecular weight and their activities are controlled by modification like phosphorylation or state of association with other subunits. For such reasons, it is impossible that they are used for stimulating laminin-332 production according to direct administration to a living body to deliver them to epidermal cells in a skin tissue. Further, as they are all regulated by a broad range of regulating factors and have a significant influence on function of a living body like inflammatory response in addition to stimulating laminin-332 production, it is hardly used routinely with safety.

PRIOR ART DOCUMENTS

Non-Patent Document

Non-Patent Document 1: Sugawara, et al., Exp Dermatol., 17(6), 473-80 (2008)

Non-Patent Document 2: Aberdam, et al., Nat. Genet., 6,299, (1994)

Non-Patent Document 3: Amano, S., SOFW J., 134:10 (2008)

Non-Patent Document 4: Amano, S., J. Investig. Dermatol. Symp. Proc., 14:2-7 (2009)

Non-Patent Document 5: Fitsialos, G., et al., J. Cell Sci., 121:2992 (2008)

Non-Patent Document 6: Zboralski, D., et al., BMC Cancer, 8:215 (2008)

DISCLOSURE OF THE INVENTION

Problem to be Solved by the Invention

Under the circumstances, there is a need to develop a composition which has a function of stimulating production of laminin-332, specifically a composition having high stability and safety that can be routinely used.

Means for Solving the Problem

The present invention provides a laminin-332 production stimulating composition comprising one or more compounds selected from the group consisting of D-alanine and D-hydroxyproline, and derivatives and/or salts thereof.

The laminin-332 production stimulating composition of the present invention may be used for suppressing and/or improving a skin condition.

Regarding the laminin-332 production stimulating composition of the present invention, the skin condition comprise, but are not limited thereto, a photoaging, wrinkles, a rough skin, fine wrinkles, and a dry skin.

The laminin-332 production stimulating composition of the present invention may be used for a pharmaceutical product.

The laminin-332 production stimulating composition of the present invention may be used for an external preparation for the skin.

The laminin-332 production stimulating composition of the present invention may be used for a food.

The present invention also provides a method of suppressing and/or improving a skin condition comprising a step of administering a laminin-332 production stimulating composition comprising one or more compounds selected from the group consisting of D-alanine and D-hydroxyproline, and derivatives and/or salts thereof.

The skin condition that is suppressed and/or improved by the method of the present invention comprises, but not limited thereto, a photoaging, wrinkles, a rough skin, fine wrinkles, and a dry skin.

According to the method of the present invention, the laminin-332 production stimulating composition may be a pharmaceutical product.

According to the method of the present invention, the composition for stimulating laminin-332 production may be an external preparation for the skin.

Regarding the method of the present invention, the composition for stimulating laminin-332 production of the invention may be used for a food composition.

As used herein, the term "salt" of D-alanine and D-hydroxyproline indicates any salt including a metal salt and an amine salt and the like, provided that the laminin-332 production stimulating effect of D-alanine and D-hydroxyproline is not impaired. The metal salt may comprise an alkaline metal salt, an alkaline earth metal salt and the like. The amine salt may comprise triethylamine salt, benzylamine salt and the like.

As used herein, the term "derivatives" of D-alanine and D-hydroxyproline indicates a D-alanine or D-hydroxyproline molecule that is covalently bound to any atomic group via its amino group, carboxy group, or side chain, provided that the laminin-332 production stimulating effect of D-alanine and D-hydroxyproline is not impaired. The atomic group comprises, but is not limited to, a protective group, such as N-phenylacetyl group, and 4,4'-dimethoxytrityl (DMT) group, a biopolymer, such as a protein, a peptide, a saccharide, a lipid, and a nucleic acid; a synthetic polymer, such as a polystyrene, a polyethylene, a polyvinyl, and a polyester; and a functional group such as an ester group. The ester group may comprise, for example, an aliphatic ester, such as methyl ester, and ethyl ester; and an aromatic ester.

An amino acid has optical isomers which are the L-form and D-form. A natural protein has L-amino acids bound by peptide bonds and only L-amino acids are employed excluding some exceptions such as a bacterial cell wall. Therefore, it has been considered that in a mammal including a human only L-amino acids are present and only L-amino acids are utilized (Kinouchi, T. et al., TANPAKUSHITSU KAKUSAN KOSO (PROTEIN, NUCLEIC ACID AND ENZYME), 50:453-460 (2005), Lehninger Principles of Biochemistry [Vol. 1] 2nd ed., pp 132-147 (1993), Japanese-language translation, Hirokawa Shoten Ltd., Harper's Biochemistry, Original version, 22nd ed., pp 21-30 (1991), Japanese-language translation, Maruzen Co., Ltd.). Accordingly, only L-amino acids have mostly been employed as amino acids academically and industrially for a long time.

Exceptional cases where a D-amino acid is employed are, for example, a case of using as a raw material for an antibiotics produced by a microorganism, and, a case of a food additive employing a D-amino acid in a DL-amino acid mixture for the purpose of reducing cost of fractionating only an L-amino acid from a mixture of the L- and D-amino acids, which are obtained in equimolar amounts by synthesizing the amino acids. Nevertheless, there has been no case of using only D-amino acids industrially as bioactive substances.

D-serine and D-aspartic acid have high ratio of D-form, and therefore many studies are performed compared to other amino acids. D-serine is localized in the cerebrum and the hippocampus, and it is known as a regulatory factor for NMDA receptor. D-aspartic acid is found to be localized in the testis or the pineal body, and it is known to be involved with control of hormone secretion (Japanese Patent Unexamined Publication No. 2005-3558). However, physiological activity of D-alanine and D-hydroxyproline in the skin has not been elucidated.

As described in the following examples, the laminin-332 production stimulating effect of D-alanine and D-hydroxyproline has been unknown so far. Thus, the laminin-332 production stimulating composition of the present invention which contains D-alanine and/or D-hydroxyproline is a novel invention.

Recently, it was reported that ddY mice were allowed to ingest freely a 10 mM aqueous solution of a D-amino acid for two weeks and then examined for the D-amino acid concentration in each organ, which was 3 to 1000 pmol per gland in the pineal body and 2 to 500 nmol per wet gram in the brain tissue (Morikawa, A. et al., Amino Acids, 32:13-20 (2007)). Based on the above, the lower limit for daily intake amount of D-alanine and D-hydroxyproline that are contained in the composition of the present invention is calculated as described below.

The D-alanine of the present invention has an effect on stimulating laminin-332 production in cultured human epidermal keratinocytes within the concentration range of from 0.1 μM (micro-molar) to 1 μM (micro-molar), as described in the following Examples. Thus, the amount of the D-alanine that is contained in the composition for improving the skin condition, the external preparation for the skin, or the food composition of the present invention may be any content, provided that the D-alanine in the above concentration range is delivered to fibroblast cells in a skin tissue in vivo. As for the external preparation for the skin of the present invention, the content of the D-alanine may be from 0.000015% by weight to 50% by weight, or up to the maximum weight concentration that can be formulated, in the total composition of the invention. Specifically, when the composition is an external preparation for the skin, the content of the D-alanine is preferably 0.00003% by weight to 30% by weight, and the most preferably 0.0003% by weight to 3% by weight. When the composition of the present invention is a pharmaceutical for internal agent, the content of the D-alanine may be within the range of 0.00001% by weight to 100% by weight. When the composition of the present invention is an internal agent, the content of the D-alanine is preferably 0.00002% by weight to 80% by weight and the most preferably 0.0002% by weight to 60% by weight. Further, the lower limit of a daily intake amount of D-alanine that is contained in the composition of the present invention may be 0.01 ng, preferably 0.1 ng, and more preferably 1 ng per 1 kg of body weight.

The D-hydroxyproline of the present invention has an effect on stimulating laminin-332 production in cultured human epidermal keratinocytes within the concentration range of 0.1 μM (micro-molar) to 1 μM (micro-molar), as described in the following Examples. Thus, the amount of the D-hydroxyproline that is contained in the formulation for improving the skin condition, the external preparation for the skin, or the food composition of the present invention may be any content, provided that the D-hydroxyproline in the above concentration range is delivered to fibroblast cells in a skin tissue in vivo. As for the external preparation for the skin of the present invention, the content of the D-hydroxyproline may be 0.000015% by weight to 50% by weight, or up to the maximum weight concentration that can be formulated, in the total composition of the invention. Specifically, when the composition is an external preparation for the skin, the content of the D-hydroxyproline is preferably 0.00003% by weight to 30% by weight, and the most preferably 0.0003% by weight to 3% by weight. When the composition of the present invention is an internal agent, the content of the D-hydroxyproline may be within the range of 0.00001% by weight to 100% by weight. When the composition of the present invention is an internal agent, the content of the D-hydroxyproline is preferably 0.00002% by weight to 80% by weight and the most preferably 0.0002% by weight to 60% by weight. Further, the lower limit of a daily intake amount of D-hydroxyproline that is contained in the composition of the present invention may be 0.01 ng, preferably 0.1 ng, and more preferably 1 ng per 1 kg of body weight.

The composition of the present invention may further comprise one or more pharmaceutically acceptable additives, in addition to D-alanine and D-hydroxyproline, salts of D-alanine and D-hydroxyproline, and/or derivatives of D-alanine and D-hydroxyproline capable of releasing D-alanine by drug metabolizing enzymes and the like in vivo, provided that the laminin-332 production stimulating effect of D-alanine and D-hydroxyproline is not impaired. Such an additive comprises, but is not limited to, a diluent and an extender, a binder and an adhesive, a lubricant, a glidant, a plasticizer, a disintegrant, a carrier solvent, a buffering agent, a colorant, a flavoring agent, a sweetener, a preservative and a stabilizer, an adsorbent, as well as other pharmaceutical additives known to those skilled in the art.

The composition of the present invention may be prepared by using, as an active ingredient, only D-alanine and D-hydroxyproline, salts of D-alanine and D-hydroxyproline, and/or derivatives of D-alanine and D-hydroxyproline capable of releasing D-alanine and D-hydroxyproline by drug metabolizing enzymes and the like in vivo. However, within the range that the effect of the present invention is not impaired, it may be appropriately formulated with other components that are used for an external preparation for the skin like cosmetics comprising quasi drugs and pharmaceutical products, if necessary. Examples of other components (i.e., optionally added components) comprise an oil, a surface active agent, a powder, a colorant, water, alcohols, a thickening agent, a chelating agent, silicones, an antioxidant, an UV absorbing agent, a moisturizing agent, a flavoring agent, various pharmaceutically effective components, a preservative, a pH adjusting agent, and a neutralizing agent.

A dosage form of a laminin-332 production stimulating composition of the present invention that is used for suppressing and/or improving the skin condition (hereinafter, referred to as an "agent for improving skin condition") may be any one that is commonly used for quasi drug compositions and pharmaceutical compositions comprising an external preparation for skin like an ointment, a cream, an emulsion, a lotion, a pack, a gel, and a patch, an oral preparation like powder, granules, a soft capsule, and a tablet, a pernasal preparation like a nasal spray, and an injection solution.

A dosage form of the external preparation for the skin according to the present invention is not specifically limited, provided that it is conventionally used for an external preparation for the skin, and it comprises an ointment, a cream, an emulsion, a lotion, a pack, a gel, and a patch.

The food composition of the present invention may further comprise, a seasoning agent, a colorant, a preservative, and other components that can be used for a food product, provided that the effect on stimulating laminin-332 production by D-alanine and D-hydroxyproline is not impaired, in addition to D-alanine and D-hydroxyproline, salts of D-alanine and D-hydroxyproline, and/or derivatives of D-alanine and D-hydroxyproline capable of releasing D-alanine and D-hydroxyproline by drug metabolizing enzymes and the like in vivo.

The food composition of the present invention may be any one employed conventionally as a food composition comprising, but not limited to, a candy, a cookie, bean paste, a French dressing, a mayonnaise, a French bread, a soy sauce, yogurt, dried seasoning powder for rice, seasoning/sauce for natto (Japanese fermented soybean), natto, unrefined black vinegar.

DESCRIPTION OF EMBODIMENTS

Examples of the present invention described below are intended only to exemplify the present invention rather than to limit the technical scope thereof. The technical scope of the present invention is limited only by the descriptions given in the claims.

All references cited herein are incorporated by reference in its entirety.

EXAMPLE 1

1. Stimulated Production of Laminin-332 by Addition of Alanine and Hydroxyproline
1-1. Materials and Methods
(1) Cells Human epidermal-derived HaCaT cells (H. Hans, et al., Experimental Cell Research, 239:399 (1998)) and human keratinocyte-derived KC cells (Sanko Junyaku Co., Ltd., manufacturer: LONZA Walkersville Inc.) were used. The cells were inoculated to a 24-well plate to have $4 \times 10^4$ cells per well. The cells were then cultured for 24 hours in a medium for cell culture (D-MEM (1 g/L glucose), manufactured by Wako Pure Chemical Industries, Ltd.) to which 0.1% bovine serum albumin (BSA) is supplemented (hereinafter, referred to as a "standard medium") in a 5% $CO_2$ and saturated water vapor atmosphere at 37° C. (degrees Celsius).

(2) Addition of Alanine and Hydroxyproline

Subsequently, the medium was switched to the standard medium to which 1 μM (micro-molar) L- or D-alanine, 0.5 μM (micro-molar) each of L- and D-alanine, 1 μM (micro-molar) L- or D-hydroxyproline, or 0.5 μM (micro-molar) each of L- and D-hydroxyproline had been added, and cultured for 24 hours. Further, the standard medium described above to which neither alanine nor hydroxyproline had been added was employed as a negative control. D-hydroxyproline used in this example was 4-cis-D-hydroxyproline.

(3) Quantification of Laminin-332 Production Amount

After completing the cell culture, culture medium was collected and centrifuged at 3000 rpm for five minutes. Concentration of laminin-332 in the supernatant was measured by ELISA (Amano, S., et al., J. Immunol. Methods, 224:161 (1999)). The ELISA used was sandwich type which utilizes biotinylated conjugate of BM165, i.e., a monoclonal antibody against α (alpha) 3 chain of laminin-5, and 6F12, i.e., a monoclonal antibody against $\beta$ (beta)$_3$ chain of laminin-5, and detection was carried out by utilizing avidin D labeled with a horseradish peroxidase (Vector Laboratories, Catalogue No. A-2004). PBS was used as a control.

(4) Quantification of Number of Viable Cells

After collecting the culture medium, the cells were washed with PBS and added with alamarBlue (trademark: Biosource International, Inc.) to have final concentration of 10%. Two hours later, according to the methods by Ahmed S. A. et al., (J. Immunol. Method., 170, 211-224 (1994)) and the instructions provided by the manufacturer, fluorescent intensity of the alamarBlue solution was measured with excitation wavelength of 544 nm and emission wavelength of 590 nm.

1-2. Results (1) Quantification of Number of Viable KC Cells

Figure 1:
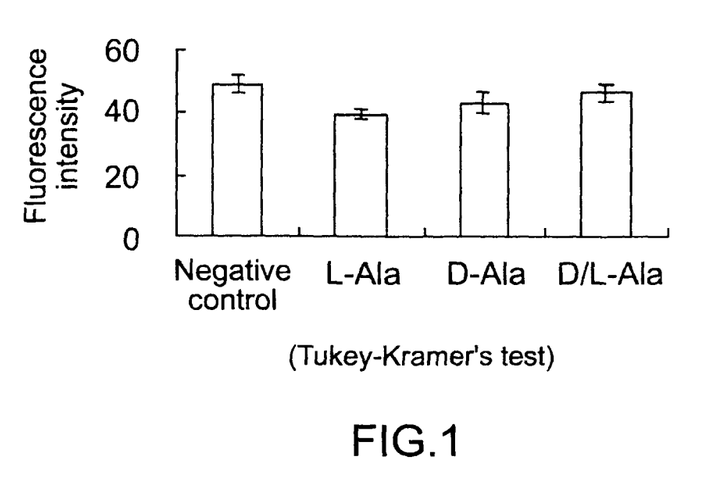
FIG. 1 is a graph illustrating the effect of D-alanine on KC cells.

FIG. 1 shows the results of the experiment obtained by examining the effect of adding alanine on proliferation of KC cells. The error bars for each experimental condition indicate the standard deviations of experimentally measured values obtained by repeating the experiment three times under the identical condition.

The relative fluorescence intensity (the same hereinafter) of alamarBlue (trademark) as a negative control was 50 in the KC cells. The fluorescence intensity of the KC cells that were cultured in the medium added with 1 μM (micro-molar) L-alanine, the medium added with 1 μM (micro-molar) D-alanine, and the medium added with 0.5 μM (micro-molar) each of L- and D-alanine were 40, 45, and 50, respectively. Compared to the negative control, the fluorescence intensity of alamarBlue (trademark) from the KC cells cultured in the medium added with alanine showed no significant difference by Tukey-Kramer's test. Thus, it was found that L- and D-alanine have no cytotoxicity against KC cells.

(2) Production of Laminin-332 in KC Cells

Figure 2:
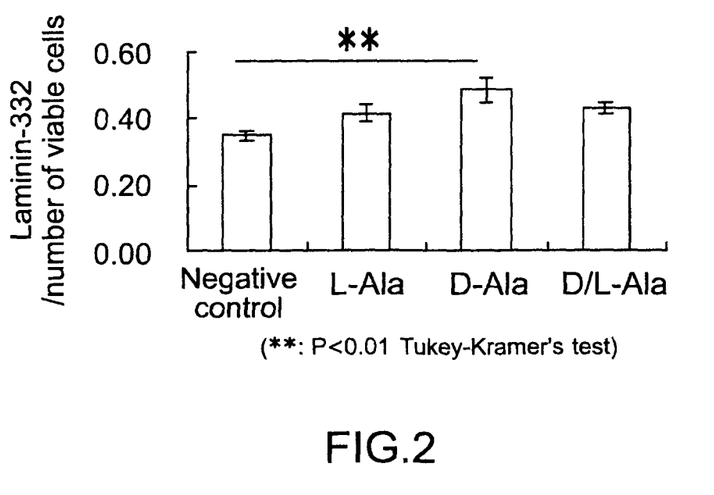
FIG. 2 is a graph illustrating the effect of D-alanine on production of laminin-332 in KC cells.

FIG. 2 shows the results of the experiment obtained by examining the effect of adding alanine on production of laminin-332 in KC cells. The vertical line of the graph in FIG. 2 represents the values obtained by dividing the absorbance obtained from ELISA measurement, which was in proportion to the concentration of laminin-332 in the culture supernatant from each well, by the fluorescence intensity of alamarBlue (trademark), which was in proportion to the number of cells present in each well (hereinafter, referred to as "relative value of laminin-332 concentration compared to the number of cells"). The error bars for each experimental condition indicate the standard deviations of experimentally measured values obtained by repeating the experiment three times under the identical condition. Further, the double asterisk (**) indicates that p is less than 1% by Tukey-Kramer's test.

The relative value of laminin-332 concentration compared to the number of cells was 0.35 in the negative control. The relative value of laminin-332 concentration compared to the number of cells in the KC cells that were cultured in the medium added with 1 μM (micro-molar) L-alanine, the medium added with 1 μM (micro-molar) D-alanine, and the medium added with 0.5 μM (micro-molar) each of L- and D-alanine were 0.40, 0.50, and 0.45, respectively. Compared to the negative control, addition of D-alanine at the concentration of 1 μM (micro-molar) resulted in p of less than 1% by Tukey-Kramer's test, demonstrating a significant difference. Thus, stimulated production of laminin-332 in KC cells by addition of D-alanine was proven.

(3) Quantification of the Number of Viable HaCaT Cells

Figure 3:
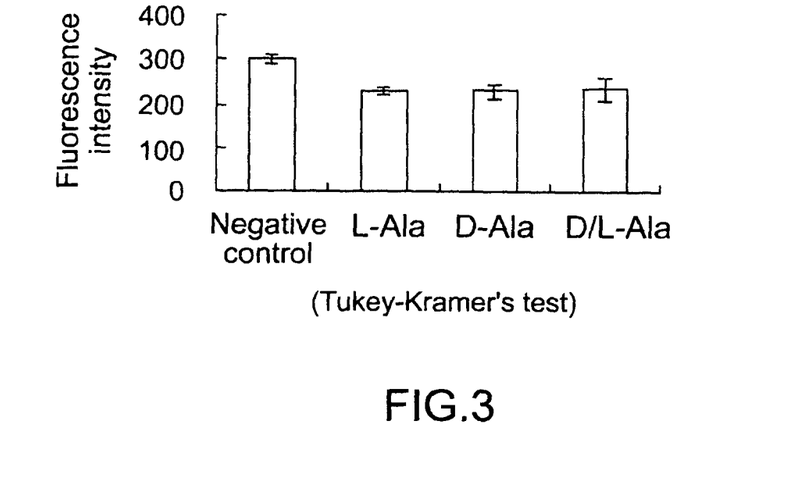
FIG. 3 is a graph illustrating the effect of D-alanine on HaCaT cells.
Figure 4:
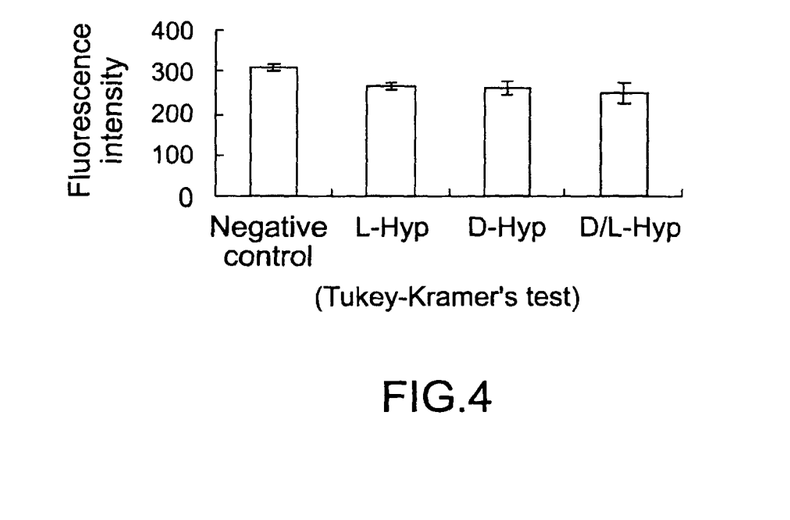
FIG. 4 is a graph illustrating the effect of D-hydroxyproline on HaCaT cells.

FIG. 3 and FIG. 4 show the results of the experiment obtained by examining the effect of adding alanine or hydroxyproline on proliferation of HaCaT cells. Hereinafter, D-hydroxyproline (D-Hyp) indicates 4-cis-D-hydroxyproline. The error bars for each experimental condition indicate the standard deviations of experimentally measured values obtained by repeating the experiment three times under the identical condition.

The fluorescence intensity of alamarBlue (trademark) as a negative control was 300 in the HaCaT cells. The fluorescence intensity of the HaCaT cells that were cultured in the medium added with 1 μM (micro-molar) L-alanine, the medium added with 1 μM (micro-molar) D-alanine, and the medium added with 0.5 μM (micro-molar) each of L- and D-alanine were all 250 (FIG. 3). The fluorescence intensity of the HaCaT cells that were cultured in the medium added with 1 μM (micro-molar) L-hydroxyproline, the medium added with 1 μM (micro-molar) D-hydroxyproline, and the medium added with 0.5 μM (micro-molar) each of L- and D-hydroxyproline were all 280 (FIG. 4). Compared to the negative control, the fluorescence intensity of alamarBlue (trademark) from the HaCaT cells cultured in the medium added with alanine or D-hydroxyproline showed no significant difference by Tukey-Kramer's test. Thus, it was found that L- and D-alanine and L- and D-hydroxyproline also have no cytotoxicity for HaCaT cells.

(4) Production of Laminin-332 in HaCaT Cells According to Alanine Addition

Figure 5:
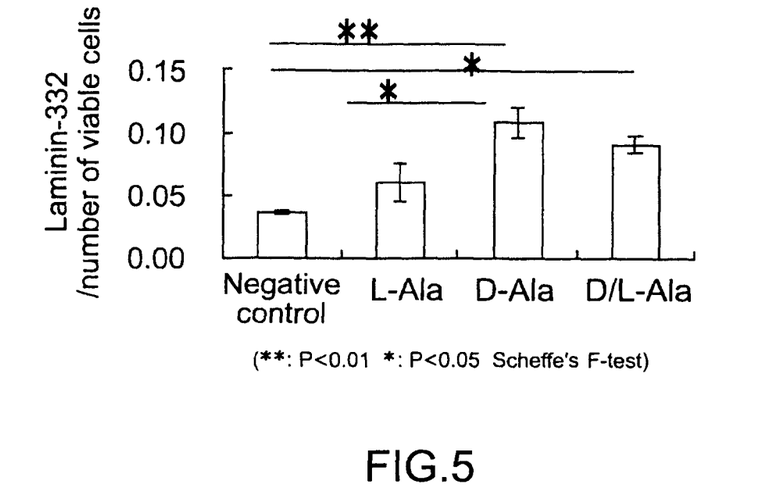
FIG. 5 is a graph illustrating the effect of D-alanine on production of laminin-332 in HaCaT cells.

FIG. 5 shows the results of the experiment obtained by examining the effect of adding alanine on production of laminin-332 in HaCaT cells. The vertical line of the graph in FIG. 5 represents, the relative values of laminin-332 concentration compared to the number of cells that are present in culture supernatant in each well. The error bars for each experimental condition indicate the standard deviations of experimentally measured values obtained by repeating the experiment three times under the identical condition. Further, the double asterisk (**) indicates that p is less than 1% and the asterisk (*) indicates that p is less than 5% by Scheffe's F test.

The relative value of laminin-332 concentration compared to the number of cells was 0.04 in the negative control. The relative value of laminin-332 concentration compared to the number of cells in the HaCaT cells cultured in the medium added with 1 μM (micro-molar) L-alanine, the medium added with 1 μM (micro-molar) D-alanine, and the medium added with 0.5 μM (micro-molar) each of L- and D-alanine were 0.07, 0.11, and 0.10, respectively. Compared to the negative control, addition of D-alanine at the concentration of 1 μM (micro-molar) resulted in p of less than 1% by Scheffe's F test. Compared to the negative control, addition of a mixture containing both D-alanine and L-alanine at the concentration of 0.5 μM (micro-molar) resulted in p of less than 5% by Scheffe's F test. The value of p was less than 5% by Scheffe's F test between 1 μM (micro-molar) D-alanine and 1 μM (micro-molar) L-alanine, thus all showed significant differences. Thus, similar to the KC cells, stimulated production of laminin-332 by addition of D-alanine was also proven in the HaCaT cells.

Figure 6:
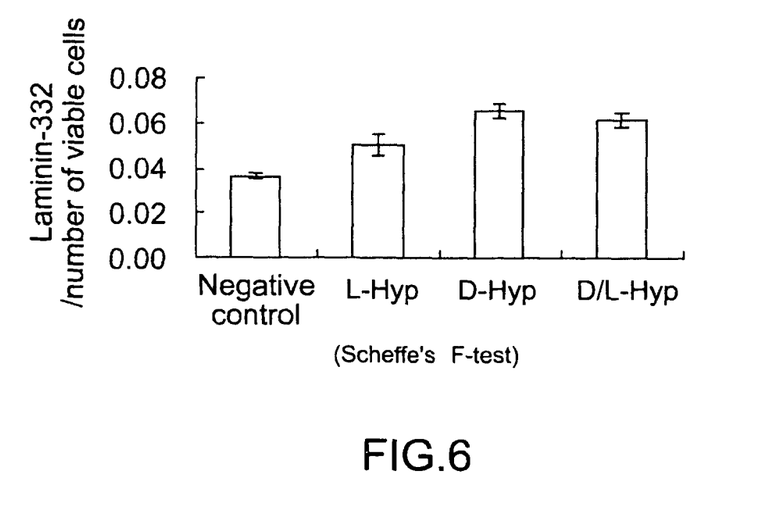
FIG. 6 is a graph illustrating the effect of D-hydroxyproline on production of laminin-332 in HaCaT cells.

(5) Production of Laminin-332 in HaCaT Cells According to Hydroxyproline Addition FIG. 6 shows the results of the experiment obtained by examining the effect of adding hydroxyproline on production of laminin-332 in HaCaT cells. The vertical line of the graph in FIG. 6 represents the relative values of laminin-332 concentration compared to the number of cells present in the culture supernatant in each well. The error bars for each experimental condition indicate the standard deviations of experimentally measured values obtained by repeating the experiment three times under the identical condition.

The relative value of laminin-332 concentration compared to the number of cells was 0.04 in the negative control. The relative values of laminin-332 concentration compared to the number of cells in the HaCaT cells cultured in the medium added with 1 μM (micro-molar) L-hydroxyproline, the medium added with 1 μM (micro-molar) D-hydroxyproline, and the medium added with 0.5 μM (micro-molar) each of L- and D-hydroxyproline were 0.05, 0.065, and 0.06, respectively.

EXAMPLE 2

2. Comparison of Production Amount of Laminin-332 According to Addition of Various Amino Acids 2-1. Materials and Methods Cell culture was carried out in the same manner as the Example 1 by using HaCaT cells. After that, the medium was switched to the standard medium added with amino acids such as L- or D-alanine, L- or D-hydroxyproline, L- or D-aspartic acid, L- or D-asparagine, L- or D-proline, or L- or D-serine with the concentration of 10 nM, 100 nM, or 1000 nM, and cultured for 24 hours. The standard medium to which no amino acid had been added was used as a negative control. D-Hydroxyproline used in this example was 4-cis-D-hydroxyproline. The production amount of laminin-332 was measured in the same manner as the Example 1. No cytotoxicity was observed for the following experiments in which amino acids had been added at various concentrations, and the production amounts of laminin-332 in the cells were compared for each experimental condition.

2-2. Results (1) Addition of Alanine

Figure 7:
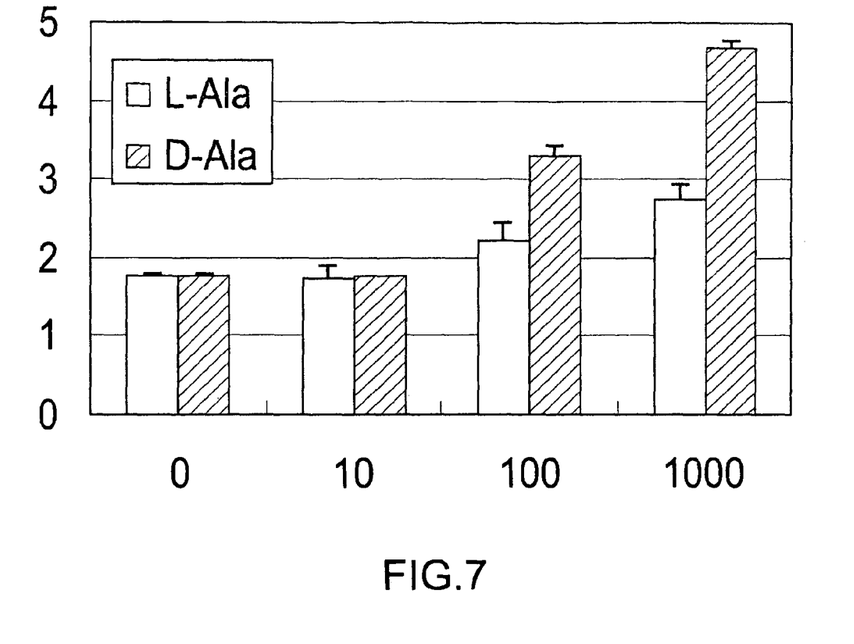
FIG. 7 is a graph illustrating the effect of D-alanine with various concentrations on production of laminin-332 in HaCaT cells.

FIG. 7 shows the results of the experiment obtained by examining the effect of adding alanine at various concentrations on production of laminin-332 in HaCaT cells. The vertical line of the graph in FIG. 7 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.7 ng/mL in the negative control. The concentration of laminin-332 in the HaCaT cells that were cultured in the medium added with alanine at the concentration of 10 nM, 100 nM, and 1000 nM were 1.7 ng/mL, 2.3 ng/mL, and 2.8 ng/mL, respectively, for L-alanine, and 1.7 ng/mL, 3.4 ng/mL, and 4.8 ng/mL, respectively, for D-alanine. Based on the results above, it was found that D-alanine can stimulate the production of laminin-332 at the concentration of 100 ng/mL or higher.

(2) Addition of Hydroxyproline

Figure 8:
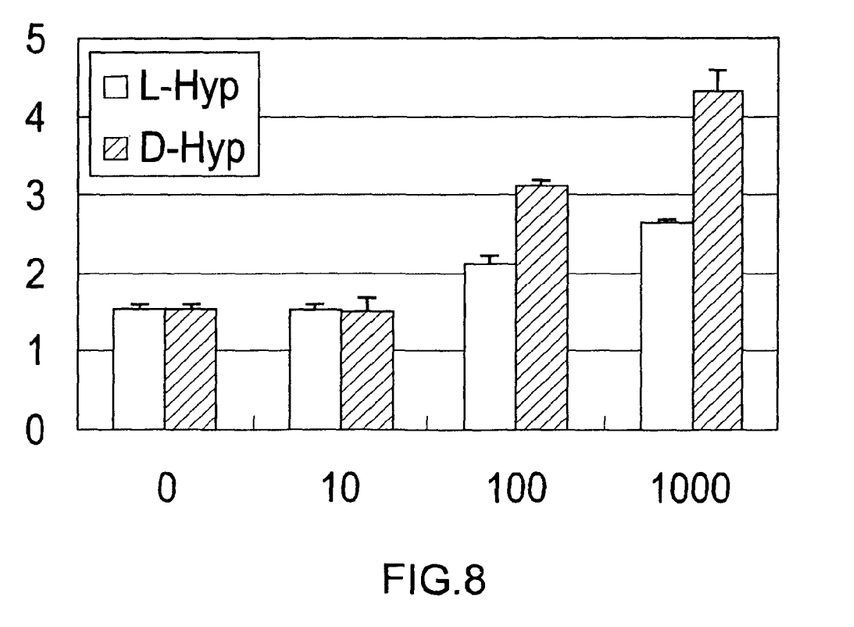
FIG. 8 is a graph illustrating the effect of D-hydroxyproline with various concentrations on production of laminin-332 in HaCaT cells.

FIG. 8 shows the results of the experiment obtained by examining the effect of adding hydroxyproline at various concentrations on production of laminin-332 in HaCaT cells. The vertical line of the graph in FIG. 8 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.5 ng/mL in the negative control. The concentration of laminin-332 in the HaCaT cells that were cultured in the medium added with hydroxyproline at the concentrations of 10 nM, 100 nM, and 1000 nM were 1.5 ng/mL, 2.3 ng/mL, and 2.7 ng/mL, respectively, for L-hydroxyproline, and 1.5 ng/mL, 3.3 ng/mL, and 4.4 ng/mL, respectively, for D-hydroxyproline. Based on the results above, it was found that D-hydroxyproline can stimulate the production of laminin-332 at the concentration of 100 ng/mL or higher.

(3) Addition of Aspartic Acid

Figure 9:
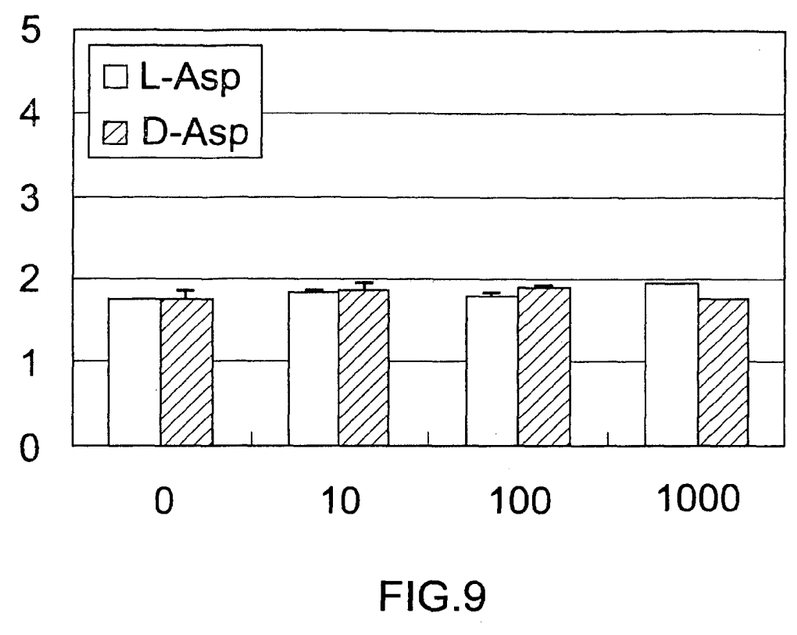
FIG. 9 is a graph illustrating the effect of D-aspartic acid with various concentrations on production of laminin-332 in HaCaT cells.

FIG. 9 shows the results of the experiment obtained by examining the effect of adding aspartic acid at various concentrations on production of laminin-332 in HaCaT cells. The vertical line of the graph in FIG. 9 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.7 ng/mL in the negative control. The concentration of laminin-332 in the HaCaT cells cultured in the medium added with aspartic acid at the concentration of 10 nM, 100 nM, and 1000 nM were 1.8 ng/mL, 1.8 ng/mL, and 2.0 ng/mL, respectively, for L-aspartic acid, and 1.9 ng/mL, 1.9 ng/mL, and 1.7 ng/mL, respectively, for D-aspartic acid. Based on the results above, it was found that both L- and D-aspartic acid do not stimulate the production of laminin-332.

(4) Addition of Asparagine

Figure 10:
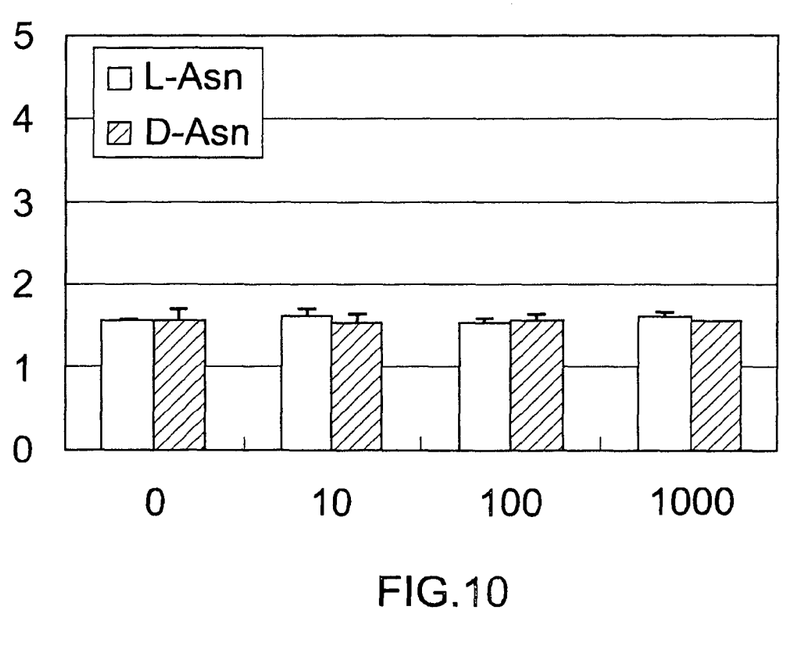
FIG. 10 is a graph illustrating the effect of D-asparagine with various concentrations on production of laminin-332 in HaCaT cells.

FIG. 10 shows the results of the experiment obtained by examining the effect of adding asparagine at various concentrations on production of laminin-332 in HaCaT cells. The vertical line of the graph in FIG. 10 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.5 ng/mL in the negative control. The concentration of laminin-332 in the HaCaT cells that had been cultured in the medium added with asparagine at the concentration of 10 nM, 100 nM, and 1000 nM were 1.6 ng/mL, 1.5 ng/mL, and 1.6 ng/mL, respectively, for L-asparagine, and 1.5 ng/mL, 1.5 ng/mL, and 1.5 ng/mL, respectively, for D-asparagine. Based on the results above, it was found that both L- and D-asparagine do not stimulate the production of laminin-332.

(5) Addition of Proline

Figure 11:
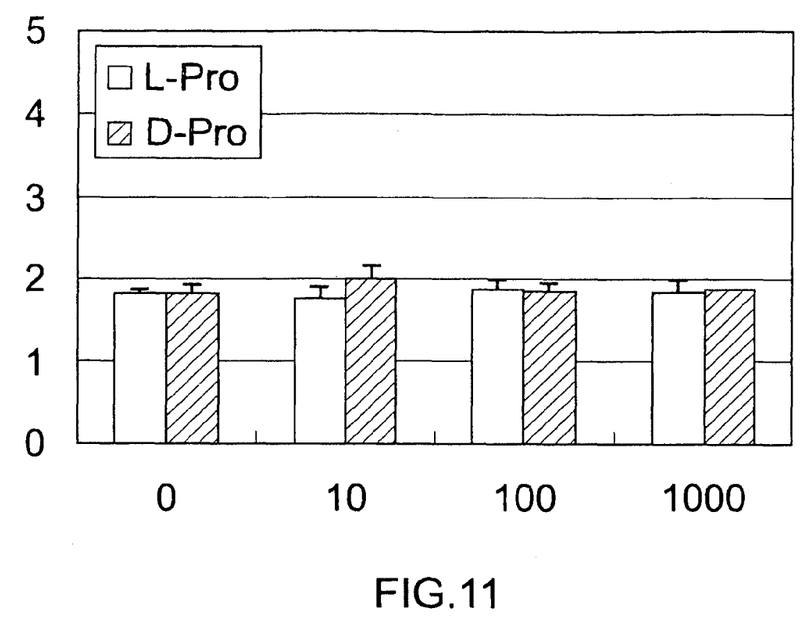
FIG. 11 is a graph illustrating the effect of D-proline with various concentrations on production of laminin-332 in HaCaT cells.

FIG. 11 shows the results of the experiment obtained by examining the effect of adding proline at various concentrations on production of laminin-332 in HaCaT cells. The vertical line of the graph in FIG. 11 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.8 ng/mL in the negative control. The concentration of laminin-332 in the HaCaT cells cultured in the medium added with proline at the concentration of 10 nM, 100 nM, and 1000 nM were 1.8 ng/mL, 1.9 ng/mL, and 1.9 ng/mL, respectively, for L-proline, and 2.0 ng/mL, 1.9 ng/mL, and 1.9 ng/mL, respectively, for D-proline. Based on the results above, it was found that both L- and D-proline do not stimulate the production of laminin-332.

(6) Addition of Serine

Figure 12:
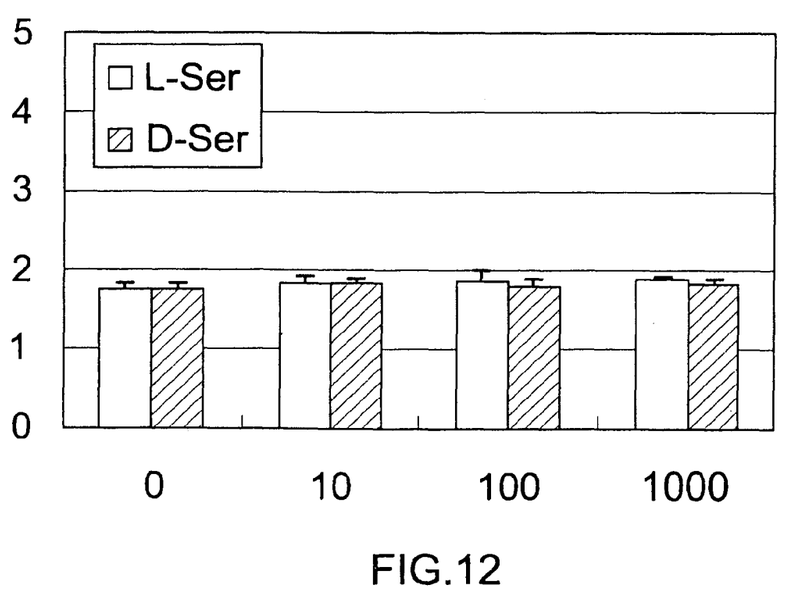
FIG. 12 is a graph illustrating the effect of D-serine with various concentrations on production of laminin-332 in HaCaT cells.

FIG. 12 shows the results of the experiment obtained by examining the effect of adding serine at various concentrations on production of laminin-332 in HaCaT cells. The vertical line of the graph in FIG. 12 represents the concentrations (ng/mL) of laminin-332 in the culture supernatant in each well. The error bars for each experimental condition indicate the standard deviations of experimentally measured values obtained by repeating the experiment four times under the identical condition.

The concentration of laminin-332 was 1.7 ng/mL in the negative control. The concentrations of laminin-332 in the HaCaT cells that were cultured in the medium added with serine at the concentration of 10 nM, 100 nM, and 1000 nM were 1.8 ng/mL, 1.9 ng/mL, and 1.9 ng/mL, respectively, for L-serine, and 1.8 ng/mL, 1.8 ng/mL, and 1.8 ng/mL, respectively, for D-serine. Based on the results above, it was found that both L- and D-serine do not stimulate the production of laminin-332.

CONCLUSIONS

Based on the experimental results obtained from the Examples 1 and 2, the effect on stimulating production of laminin-332 was observed for D-alanine and D-hydroxyproline. However, no such effect was observed for aspartic acid, asparagine, proline, and serine. As a result, it was demonstrated that D-alanine and D-hydroxyproline can be used for suppressing and/or improving the skin condition by stimulating production of laminin-332, which plays an important role for maintaining structure and function of the basal membrane.

EXAMPLE 3

Formulation examples of a composition comprising D-alanine and/or D-hydroxyproline according to the present invention, i.e., an emulsion preparation, a patch, a tablet, a soft capsule, a granule, a beverage, a candy, a cookie, bean paste, a French dressing, a mayonnaise, a French bread, a soy sauce, yogurt, dried seasoning powder for rice, seasoning/sauce for natto, natto, unrefined black vinegar, cream, body cream, gel, a peel-off mask, a wet pack, an emulsion, a cosmetic water, and an aerosol preparation, are given below. These formulation examples are all illustrative and not intended to limit the technical scope of the present invention.

FORMULATION EXAMPLE 1

Emulsion Preparation

| (Composition) | Content (% by weight) |
| --- | --- |
| D-Alanine or D-hydroxyproline | 0.42 |
| Behenyl alcohol | 0.2 |
| Cetanol | 0.5 |
| Glycerin monofatty acid ester | 1.8 |
| Hydrogenated castor oil POE (60) | 1.0 |
| White petrolatum | 2.0 |
| Liquid paraffin | 10.0 |
| Isopropyl myristate | 3.0 |
| Methyl polysiloxane (6cs) | 1.5 |
| Concentrated glycerin | 13.0 |
| Dipropylene glycol | 2.0 |
| Carboxyvinyl polymer | 0.25 |
| Sodium hyaluronate | 0.005 |
| Potassium hydroxide | Proper quantity |
| Lactic acid | Proper quantity |
| Edetate sodium | Proper quantity |
| Ethylparaben | Proper quantity |
| Purified water | Remainder |
| | 100.000 |

FORMULATION EXAMPLE 2

Patch

| (Composition) | Content (% by weight) |
| --- | --- |
| D-Alanine or D-hydroxyproline | 0.3 |
| Polyacrylic acid | 3.0 |
| Sodium polyacrylate | 2.5 |
| Gelatin | 0.5 |
| Sodium carboxymethyl cellulose | 4.0 |
| Polyvinyl alcohol | 0.3 |
| Concentrated glycerin | 14.0 |
| 1,3-Butylene glycol | 12.0 |
| Aluminum hydroxide | 0.1 |
| Edetate sodium | 0.03 |
| Methylparaben | 0.1 |
| Purified water | Remainder |
| | 100.00 |

FORMULATION EXAMPLE 3

Tablet

| (Composition) | Content (mg/tablet) |
| --- | --- |
| D-Alanine or D-hydroxyproline | 360.5 |
| Lactose | 102.4 |
| Calcium carboxymethyl | 29.9 |

-continued

| (Composition) | Content (mg/tablet) |
|---|---|
| cellulose | |
| Hydroxypropyl cellulose | 6.8 |
| Magnesium stearate | 5.2 |
| Crystalline cellulose | 10.2 |
| | 515.0 |

FORMULATION EXAMPLE 4

Tablet

| (Composition) | Content (mg/tablet) |
|---|---|
| Sucrose ester | 70 |
| Crystalline cellulose | 74 |
| Methyl cellulose | 36 |
| Glycerin | 25 |
| D-Alanine or D-hydroxyproline | 475 |
| N-Acetylglucosamine | 200 |
| Hyaluronic acid | 150 |
| Vitamin E | 30 |
| Vitamin B6 | 20 |
| Vitamin B2 | 10 |
| α (alpha)-Lipoic acid | 20 |
| Coenzyme Q10 | 40 |
| Ceramide (Konjac extract) | 50 |
| L-Proline | 300 |
| | 1500 |

FORMULATION EXAMPLE 5

Soft Capsule

| (Composition) | Content (mg/capsule) |
|---|---|
| Edible soybean oil | 530 |
| *Eucommia ulmoides* extract | 50 |
| *Ginseng* extract | 50 |
| D-Alanine or D-hydroxyproline | 100 |
| Royal jelly | 50 |
| Maca | 30 |
| GABA | 30 |
| Beeswax | 60 |
| Gelatin | 375 |
| Glycerin | 120 |
| Glycerin fatty acid ester | 105 |
| | 1500 |

FORMULATION EXAMPLE 6

Soft Capsule

| (Composition) | Content (mg/capsule) |
|---|---|
| Brown rice germ oil | 659 |
| D-Alanine or D-hydroxyproline | 500 |
| Resveratrol | 1 |
| *Lotus* germ extract | 100 |
| Elastin | 180 |
| DNA | 30 |
| Folic acid | 30 |
| | 1500 |

FORMULATION EXAMPLE 7

Granule

| (Composition) | Content (mg/pack) |
|---|---|
| D-Alanine or D-hydroxyproline | 400 |
| Vitamin C | 100 |
| Soybean isoflavone | 250 |
| Reduced lactose | 300 |
| Soybean oligosaccharide | 36 |
| Erythritol | 36 |
| Dextrin | 30 |
| Flavoring agent | 24 |
| Citric acid | 24 |
| | 1200 |

FORMULATION EXAMPLE 8

Beverage

| (Composition) | Content (g/60 mL) |
|---|---|
| *Eucommia ulmoides* extract | 1.6 |
| *Ginseng* extract | 1.6 |
| D-Alanine or D-hydroxyproline | 1.6 |
| Reduced maltose syrup | 28 |
| Erythritol | 8 |
| Citric acid | 2 |
| Flavoring agent | 1.3 |
| N-Acetylglucosamine | 1 |
| Sodium hyaluronate | 0.5 |
| Vitamin E | 0.3 |
| Vitamin B6 | 0.2 |
| Vitamin B2 | 0.1 |
| α (alpha)-Lipoic acid | 0.2 |
| Coenzyme Q10 | 1.2 |
| Ceramide (Konjac extract) | 0.4 |
| L-proline | 2 |
| Purified water | Remainder |
| | 60 |

FORMULATION EXAMPLE 9

Candy

| (Composition) | Content (% by weight) |
|---|---|
| Sugar | 50 |
| Syrup | 48 |
| D-Alanine or D-hydroxyproline | 1 |
| Flavoring agent | 1 |
| | 100 |

FORMULATION EXAMPLE 10

Cookie

| (Composition) | Content (% by weight) |
|---|---|
| Weak flour | 45.0 |
| Butter | 17.5 |
| Granulated sugar | 20.0 |
| D-Alanine or D-hydroxyproline | 4.0 |
| Egg | 12.5 |
| Flavoring agent | 1.0 |
| | 100.0 |

Method for producing Formulation Example 10 (Cookie)

Granulated sugar is added slowly to butter while stirring, to which an egg, a flavoring agent, and D-alanine or D-hydroxyproline are added and stirred. After mixing thoroughly, uniformly sieved weak flour is added and stirred at a low speed, and allowed to stand as a bulk in a refrigerator. Thereafter, it is molded and baked for 15 minutes at 170° C. (degrees Celsius) to obtain a cookie.

FORMULATION EXAMPLE 11

Bean Paste

| (Composition) | Content (g) |
|---|---|
| Soybean | 1000 |
| Malted rice | 1000 |
| Salt | 420 |
| D-Alanine or D-hydroxyproline | 158 |
| Water | Remainder |
| | 4000 |

Method for Producing Formulation Example 11 (Bean Paste)

Malted rice is mixed thoroughly with a salt. Washed soybeans are soaked overnight in three times its volumes of water, which are then drained off, and new water is added while boiling, and poured into a colander to collect the broth (tanemizu fluid), to which D-alanine or D-hydroxyproline is dissolved at 10% w/v. The boiled beans are minced immediately, combined with malted rice mixed with salt, to which the tanemizu fluid containing D-alanine or D-hydroxyproline dissolved therein is added and kneaded evenly to obtain a clay-like hardness. Dumplings are made and stuffed in a container compactly without forming any voids, and the surface of the content is smoothened and sealed with a plastic film. After three months, the content is transferred to a new container and the surface is smoothened and sealed with a plastic film. Instead of adding D-alanine or D-hydroxyproline to the tanemizu fluid, a malted rice producing a large amount of D-alanine or D-hydroxyproline may be employed. Such malted rice can be selected by quantifying D-alanine or D-hydroxyproline by the method described in Japanese Patent Unexamined Publication No. 2008-185558. Alternatively, a commercially available bean paste can be supplemented with D-alanine or D-hydroxyproline or a salt thereof.

FORMULATION EXAMPLE 12

French Dressing

| (Composition) | Content (g) |
|---|---|
| Salad oil | 27.0 |
| Vinegar | 30.0 |
| Sodium chloride | 0.9 |
| D-Alanine or D-hydroxyproline | 1.1 |
| Pepper | 1.0 |
| | 60.0 |

Method for Producing Formulation Example 12 (French Dressing)

Vinegar is combined with sodium chloride and D-alanine or D-hydroxyproline, and then stirred thoroughly to be dissolved. Salad oil is added to the mixture and the mixture is stirred thoroughly and then pepper is added.

FORMULATION EXAMPLE 13

Mayonnaise

| (Composition) | Content (g) |
|---|---|
| Salad oil | 134.0 |
| Vinegar | 5 |
| Sodium chloride | 0.9 |
| D-Alanine or D-hydroxyproline | 1 |
| Egg yolk | 18 |
| Sugar | 0.2 |
| Pepper | 0.9 |
| | 160.0 |

Method for Producing Formulation Example 13 (Mayonnaise)

Vinegar, sodium chloride, pepper, and D-alanine or D-hydroxyproline are added to egg yolk (room temperature) and stirred thoroughly by using a whisk. Stirring is continued while adding salad oil in portions to form an emulsion. Finally, sugar is added and the mixture is stirred.

FORMULATION EXAMPLE 14

French Bread

| (Composition) | Content (g) |
|---|---|
| Hard flour | 140 |
| Weak flour | 60 |
| Sodium chloride | 3 |
| Sugar | 6 |
| D-Alanine or D-hydroxyproline | 2 |
| Dry yeast | 4 |
| Lukewarm water | 128 |
| | 343 |

Method for Producing Formulation Example 14 (French Bread)

Lukewarm water is combined with 1 g of sugar and dry yeast, which is then allowed to undergo a pre-fermentation. Hard flour, weak flour, sodium chloride, 5 g of sugar and D-alanine or D-hydroxyproline are added in a bowl, into which the pre-fermented yeast is added. After kneading thoroughly into a ball-like dough, a primary fermentation is conducted at 30° C. (degrees Celsius). The dough is kneaded again and allowed to stand, and then shaped into suitable forms, which are subjected to a final fermentation using an electronic fermentation machine. After forming coupes, baking is carried out for 30 minutes in an oven at 220° C. (degrees Celsius).

FORMULATION EXAMPLE 15

Soy Sauce

| (Composition) | Content (g) |
|---|---|
| Commercially available soy sauce | 900 |
| D-Alanine or D-hydroxyproline | 100 |
| | 1000 |

Method for Producing Formulation Example 15 (Soy Sauce)

Commercially available soy sauce is added with D-alanine or D-hydroxyproline, or a salt thereof, and stirred thoroughly. Instead of adding D-alanine or D-hydroxyproline or a salt thereof, malted rice producing a large amount of D-alanine or D-hydroxyproline may be employed for fermenting soy sauce. Such malted rice can be selected by quantifying D-alanine or D-hydroxyproline by the method described in Japanese Patent Unexamined Publication No. 2008-185558.

FORMULATION EXAMPLE 16

Yogurt

| (Composition) | Content (g) |
|---|---|
| Milk | 880 |
| L. bulgaricus | 50 |
| S. thermophilus | 50 |
| D-Alanine or D-hydroxyproline | 20 |
| | 1000 |

Method for Producing Formulation Example 16 (Yogurt)

Fermentation is conducted at 40° C. (degrees Celsius) to 45° C. (degrees Celsius). Other commercially available fermentation seed organisms may be employed and commercially available yogurt may be supplemented with D-alanine, D-hydroxyproline, or a salt thereof. Instead of adding D-alanine, D-hydroxyproline or a salt thereof, an organism producing a large amount of D-alanine or D-hydroxyproline may be employed. Such an organism can be selected by quantifying D-alanine or D-hydroxyproline by the method described in Japanese Patent Unexamined Publication No. 2008-185558.

FORMULATION EXAMPLE 17

Dried Seasoning Powder for Rice

| (Composition) | Content (g) |
|---|---|
| D-Alanine or D-hydroxyproline | 50 |
| Laver | 15 |
| Sodium L-glutamate | 10 |
| Sodium chloride | 2 |
| Roasted sesame | 10 |
| Dried mackerel shavings | 10 |
| Sugar | 1 |
| Soy sauce | 2 |
| | 100 |

FORMULATION EXAMPLE 18

Seasoning/Sauce for Natto

| (Composition) | Content (g) |
|---|---|
| Commercially available sauce for natto | 9 |
| D-Alanine or D-hydroxyproline | 1 |
| | 10 |

FORMULATION EXAMPLE 19

Natto

| (Composition) | Content (g) |
| --- | --- |
| Commercially available natto | 19.9 |
| D-Alanine or D-hydroxyproline | 0.1 |
| | 20 |

Method for Producing Formulation Example 19 (Natto)

Commercially available natto is added with D-alanine or D-hydroxyproline, or a salt thereof, and stirred thoroughly. Instead of adding D-alanine or D-hydroxyproline, or a salt thereof, an organism producing a large amount of D-alanine or D-hydroxyproline may be employed for producing natto. Such an organism can be selected by quantifying D-alanine or D-hydroxyproline by the method described in Japanese Patent Unexamined Publication No. 2008-185558.

FORMULATION EXAMPLE 20

Unrefined Black Vinegar

| (Composition) | Content (g) |
| --- | --- |
| Commercially available unrefined black vinegar | 900 |
| D-Alanine or D-hydroxyproline | 100 |
| | 1000 |

Method for Producing Formulation Example 20 (Unrefined Black Vinegar)

Commercially available unrefined black vinegar is added with D-alanine or D-hydroxyproline, or a salt thereof, and stirred thoroughly. Instead of adding D-alanine or D-hydroxyproline or a salt thereof, an organism producing a large amount of D-alanine or D-hydroxyproline may be employed for producing vinegar, black vinegar or unrefined vinegar. Such an organism can be selected by quantifying D-alanine or D-hydroxyproline by the method described in Japanese Patent Unexamined Publication No. 2008-185558.

FORMULATION EXAMPLE 21

Cream

| (Composition) | Content (% by weight) |
| --- | --- |
| Liquid paraffin | 3 |
| White petrolatum | 1 |
| Dimethyl polysiloxane | 1 |
| Stearyl alcohol | 1.8 |
| Behenyl alcohol | 1.6 |
| Glycerin | 8 |
| Dipropylene glycol | 5 |
| *Macadamia* nut oil | 2 |
| Hydrogenated oil | 3 |
| Squalane | 6 |
| Stearic acid | 2 |

-continued

| (Composition) | Content (% by weight) |
| --- | --- |
| Cholesteryl hydroxystearate acid | 0.5 |
| Cetyl 2-ethylhexanoate | 4 |
| Polyoxyethylene hydrogenated castor oil | 0.5 |
| Self-emulsifying glyceryl monostearate | 3 |
| Potassium hydroxide | 0.15 |
| Sodium hexametaphosphate | 0.05 |
| Trimethyl glycine | 2 |
| Potassium ascorbyl tocopheryl phosphate | 1 |
| Tocopheryl acetate | 0.1 |
| D-Alanine or D-hydroxyproline | 4 |
| Paraben | Proper quantity |
| Edetate trisodium | 0.05 |
| 4-t-Butyl-4'-methoxy dibenzoylmethane | 0.05 |
| Glyceryl ethylhexanoate dimethoxycinnamate | 0.05 |
| Colorant | Proper quantity |
| Carboxyvinyl polymer | 0.05 |
| Purified water | Remainder |
| | 100.00 |

FORMULATION EXAMPLE 22

Body Cream

| (Composition) | Content (% by weight) |
| --- | --- |
| Dimethyl polysiloxane | 3 |
| Decamethyl cyclopentasiloxane | 13 |
| Dodecamethyl cyclohexasiloxane | 12 |
| Polyoxyethylene methylpolysiloxane copolymer | 1 |
| Ethanol | 2 |
| Isopropanol | 1 |
| Glycerin | 3 |
| Dipropylene glycol | 5 |
| Polyethylene glycol 6000 | 5 |
| Sodium hexametaphosphate | 0.05 |
| Tocopheryl acetate | 0.1 |
| D-Alanine or D-hydroxyproline | 5 |
| *Foeniculum vulgare* (Fennel) extract | 0.1 |
| *Hamamelis virginiana* (Witch Hazel) extract | 0.1 |
| Ginseng extract | 0.1 |
| L-Menthol | Proper quantity |
| Paraoxybenzoic acid ester | Proper quantity |
| Edetate trisodium | 0.05 |
| Dimorpholinopyridazinone | 0.01 |
| Isopentyl trimethoxycinnamate trisiloxane | 0.1 |
| Iron oxide yellow | Proper quantity |
| Cobalt titanate | Proper quantity |
| Dimethyl distearyl ammonium hectorite | 1.5 |
| Polyvinyl alcohol | 0.1 |
| Hydroxyethyl cellulose | 0.1 |
| Trimethylsiloxy silicate | 2 |
| Flavoring agent | Proper quantity |
| Purified water | Remainder |
| | 100.00 |

FORMULATION EXAMPLE 23

Gel

| (Composition) | Content (% by weight) |
|---|---|
| Dimethyl polysiloxane | 5 |
| Glycerin | 2 |
| 1,3-Butylene glycol | 5 |
| Polyethylene glycol 1500 | 3 |
| Polyethylene glycol 20000 | 3 |
| Cetyl ethylhexanoate | 3 |
| Citric acid | 0.01 |
| Sodium citrate | 0.1 |
| Sodium hexametaphosphate | 0.1 |
| Dipotassium glycyrrhizinate | 0.1 |
| D-Alanine or D-hydroxyproline | 2 |
| Tocopheryl acetate | 0.1 |
| *Scutellaria Baicalensis* root extract | 0.1 |
| *Saxifraga sarmentos* extract | 0.1 |
| Edetate trisodium | 0.1 |
| Xanthan gum | 0.3 |
| Acrylates/C10-30 alkyl acrylate crosspolymer (Pemulen TR-2) | 0.05 |
| Agar powder | 1.5 |
| Phenoxyethanol | Proper quantity |
| Dibutylhydroxytoluene | Proper quantity |
| Purified water | Remainder |
| | 100.00 |

FORMULATION EXAMPLE 24

Peel-off Mask

| (Composition) | Content (% by weight) |
|---|---|
| Ethanol | 10 |
| 1,3-Butylene glycol | 6 |
| Polyethylene glycol 4000 | 2 |
| Olive oil | 1 |
| *Macadamia* nut oil | 1 |
| Phytosteryl hydroxystearic acid | 0.05 |
| Lactic acid | 0.05 |
| Sodium lactate | 0.1 |
| Disodium ascorbyl sulfate | 0.1 |
| Potassium ascorbyl tocopheryl phosphate | 0.1 |
| D-Alanine or D-hydroxyproline | 10 |
| Fish collagen | 0.1 |
| Sodium chondroitin sulfate | 0.1 |
| Sodium carboxymethyl cellulose | 0.2 |
| Polyvinyl alcohol | 12 |
| Paraoxybenzoic acid ester | Proper quantity |
| Flavoring agent | Proper quantity |
| Purified water | Remainder |
| | 100.00 |

FORMULATION EXAMPLE 25

Wet Pack

| (Composition) | Content (% by weight) |
|---|---|
| Glycerin | 1 |
| 1,3-Butylene glycol | 8 |
| Xylit | 2 |
| Polyethylene glycol 1500 | 2 |
| Rosemary oil | 0.01 |
| Sage oil | 0.1 |
| Citric acid | 0.02 |
| Sodium citrate | 0.08 |
| Sodium hexametaphosphate | 0.01 |
| Hydroxypropyl-β(beta)-cyclodextrin | 0.1 |
| D-Alanine or D-hydroxyproline | 0.5 |
| Birch extract | 0.1 |
| Lavender oil | 0.01 |
| Xanthane gum | 0.05 |
| Carboxylvinyl polymer | 0.15 |
| Paraoxybenzoic acid ester (Paraben) | Proper quantity |
| Purified water | Remainder |
| | 100.00 |

FORMULATION EXAMPLE 26

Emulsion

| (Composition) | Content (% by weight) |
|---|---|
| Liquid paraffin | 7 |
| White petrolatum | 3 |
| Decamethyl cyclopentasiloxane | 2 |
| Behenyl alcohol | 1.5 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra (2-ethylhexanoate) | 3 |
| Cetyl 2-ethylhexanoate | 3 |
| Monostearic acid glycerin | 1 |
| Polyoxyethylene-glycerin monostearate | 1 |
| Potassium hydroxide | 0.1 |
| Sodium hexametaphosphate | 0.05 |
| Stearyl glycyrrhetinate | 0.05 |
| D-Alanine or D-hydroxyproline | 1 |
| Royal jelly extract | 0.1 |
| Yeast extract | 0.1 |
| Tocopheryl acetate | 0.1 |
| Acetylated sodium hyaluronate | 0.1 |
| Edetate trisodium | 0.05 |
| 4-t-Butyl-4'-methoxydibenzoyl methane | 0.1 |
| 2-Ethylhexyl paramethoxycinnamate | 0.1 |
| Carboxylvinyl polymer | 0.15 |
| Paraben | Proper quantity |
| Flavoring agent | Proper quantity |
| Purified water | Remainder |
| | 100.00 |

FORMULATION EXAMPLE 27

Emulsion

| (Composition) | Content (% by weight) |
|---|---|
| Dimethyl polysiloxane | 2 |
| Behenyl alcohol | 1 |
| Batyl alcohol | 0.5 |
| Glycerin | 5 |
| 1,3-Butylene glycol | 7 |
| Erythritol | 2 |
| Hydrogenated oil | 3 |
| Squalane | 6 |
| Pentaerythritol tetra (2-ethylhexanoate) | 2 |
| Polyoxyethylene glyceryl isostearate | 1 |
| Polyoxyethylene glyceryl monostearate | 1 |
| D-Alanine or D-hydroxyproline | 0.3 |
| Potassium hydroxide | Proper quantity |
| Sodium hexametaphosphate | 0.05 |
| Phenoxyethanol | Proper quantity |
| Carboxyvinyl polymer | 0.1 |
| Purified water | Remainder |
| | 100.00 |

FORMULATION EXAMPLE 28

Skin Lotion

| (Composition) | Content (% by weight) |
|---|---|
| Ethyl alcohol | 5 |
| Glycerin | 1 |
| 1,3-Butylene glycol | 5 |
| Polyoxyethylene polyoxypropylene decyl tetradecyl ether | 0.2 |
| Sodium hexametaphosphate | 0.03 |
| Trimethyl glycine | 1 |
| Sodium polyasparaginate | 0.1 |
| Potassium ascorbyl tocopheryl phosphate | 0.1 |
| Thiotaurine | 0.1 |
| D-Alanine or D-hydroxyproline | 8 |
| Edetate trisodium | 0.1 |
| Carboxyvinyl polymer | 0.05 |
| Potassium hydroxide | 0.02 |
| Phenoxyethanol | Proper quantity |
| Flavoring agent | Proper quantity |
| Purified water | Remainder |
| | 100.00 |

FORMULATION EXAMPLE 29

Skin Lotion

| (Composition) | Content (% by weight) |
|---|---|
| Ethyl alcohol | 10 |
| Dipropylene glycol | 1 |
| Polyethylene glycol 1000 | 1 |
| Polyoxyethylene methyl glucoside | 1 |
| Jojoba oil | 0.01 |
| Glyceryl tri(2-ethylhexanoate) | 0.1 |
| Polyoxyethylene hydrogenated castor oil | 0.2 |
| Polyglyceryl diisostearic acid | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| L-Ascorbic acid-2-glucoside | 2 |
| D-Alanine or D-hydroxyproline | 0.5 |
| Edetate trisodium | 0.05 |
| Octyl 4-methoxycinnamate | 0.01 |
| Dibutylhydroxy toluene | Proper quantity |
| Paraben | Proper quantity |
| Deep sea water | 3 |
| Flavoring agent | Proper quantity |
| Purified water | Remainder |
| | 100.00 |

FORMULATION EXAMPLE 30

Stock Solution of Aerosol Urea Preparation for External Use

| (Composition) | Content (% by weight) |
|---|---|
| Ethyl alcohol | 15.0 |
| Polyoxyethylene hydrogenated castor oil 50 | 1.5 |
| Diphenhydramine | 1.0 |
| Dibucaine | 2.0 |
| Tocopheryl acetate | 0.5 |
| D-Alanine or D-hydroxyproline | 0.1 |
| Isostearic acid | 0.1 |
| 1,3-Butylene glycol | 3.0 |
| Polyethylene glycol 400 | 3.0 |
| Camphor | 0.05 |
| Urea | 20.0 |
| Purified water | Remainder |
| | 100.00 |

FORMULATION EXAMPLE 31

Aerosol Urea Spray

| (Composition) | Content (% by weight) |
|---|---|
| Stock solution of aerosol urea preparation for external use | 65.0 |
| Dimethyl ether | 35.0 |
| | 100.00 |

Method of Filling Formulation Example 31 (Aerosol Urea Spray)

Stock solution of an aerosol urea preparation for external use and dimethyl ether are filled in a pressure resistant aerosol aluminum can of which internal surface is coated with Teflon (registered trade mark) to prepare an aerosol preparation.

The invention claimed is:

1. A method of suppressing and/or improving a skin condition caused by a decrease in production of laminin-332 in a subject in need thereof comprising administering to the subject in need thereof, a composition comprising a laminin-332 production stimulating composition consisting essentially of D-alanine or salts thereof.

2. The method according to claim 1, wherein the skin condition comprises photoaging, wrinkles, a rough skin, fine wrinkles, and dry skin.

3. The method according to claim 1, wherein the composition comprising a composition for stimulating laminin-332 production is a pharmaceutical product.

4. The method according to claim 1, wherein the composition comprising a composition for stimulating laminin-332 production is an external preparation for the skin.

5. The method according to claim 1, wherein the composition comprising a composition for stimulating the laminin-332 production is a food composition.

* * * * *